(12) United States Patent
Quill et al.

(10) Patent No.: US 11,903,827 B1
(45) Date of Patent: *Feb. 20, 2024

(54) PROSTHETIC HEART VALVES

(71) Applicant: Anteris Technologies Corporation, Eagan, MN (US)

(72) Inventors: Jason Quill, Forest Lake, MN (US); William Leon Neethling, Booragoon (AU); Christopher B. Brodeur, Plymouth, MN (US); Ramji Iyer, Plymouth, MN (US); Kaitlyn Roth, Plymouth, MN (US)

(73) Assignee: Anteris Technologies Corporation, Eagan, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/132,708

(22) Filed: Apr. 10, 2023

Related U.S. Application Data (63) Continuation of application No. 17/957,675, filed on Sep. 30, 2022, now Pat. No. 11,622,853.

(51) Int. Cl.
*A61F 2/24* (2006.01)

(52) U.S. Cl.
CPC .......... *A61F 2/2418* (2013.01); *A61F 2/2412* (2013.01); *A61F 2220/0075* (2013.01)

(58) Field of Classification Search
CPC .............................. A61F 2/2418; A61F 2/2412
See application file for complete search history.

(56) References Cited

U.S. PATENT DOCUMENTS

| | | | |
|---|---|---|---|
| 4,624,822 | A | 11/1986 | Arru et al. |
| 5,855,601 | A | 1/1999 | Bessler et al. |
| 6,491,511 | B1 | 12/2002 | Duran et al. |
| 6,682,559 | B2 | 1/2004 | Myers et al. |
| 7,025,780 | B2 | 4/2006 | Gabbay |
| 7,087,079 | B2 | 8/2006 | Navia et al. |

(Continued)

FOREIGN PATENT DOCUMENTS

| | | |
|---|---|---|
| CN | 203736349 | 7/2014 |
| EP | 2777618 | 9/2014 |

(Continued)

OTHER PUBLICATIONS

International Search Report and Written Opinion in International Appln. No. PCT/US2018/050669, dated Nov. 26, 2018, 10 pages.

(Continued)

*Primary Examiner* — Suba Ganesan
(74) *Attorney, Agent, or Firm* — Fish & Richardson P.C.

(57) ABSTRACT

This document provides devices and methods for the treatment of heart conditions. For example, this document provides prosthetic heart valves and transcatheter heart valve replacement methods. The prosthetic heart valves can be configured into a low-profile configuration for containment within a small diameter delivery sheath. The prosthetic heart valves include can include a valve member attached to a stent frame. In some embodiments, the valve member is a molded biomaterial with a novel shape and resulting performance characteristics. Localized protective covering members can be attached to the stent frame to prevent the valve member from contacting the stent frame as the valve member cycles between its open and closed configurations.

40 Claims, 6 Drawing Sheets

(56) References Cited

U.S. PATENT DOCUMENTS

| | | |
|---|---|---|
| 8,778,018 B2 | 7/2014 | Iobbi |
| 8,992,599 B2 | 3/2015 | Thubrikar et al. |
| 9,011,525 B2 | 4/2015 | Claiborne, III et al. |
| 9,095,430 B2 | 8/2015 | Cunanan et al. |
| 9,192,470 B2 | 11/2015 | Cai et al. |
| 9,205,172 B2 | 12/2015 | Neethling et al. |
| 9,259,313 B2 | 2/2016 | Wheatley |
| 9,301,835 B2 | 4/2016 | Campbell et al. |
| 9,554,902 B2 | 1/2017 | Braido et al. |
| 9,744,037 B2 | 8/2017 | Kheradvar et al. |
| 9,763,780 B2 | 9/2017 | Morriss et al. |
| 11,135,059 B2 | 10/2021 | Hammer et al. |
| 11,464,635 B2 | 10/2022 | Reimer et al. |
| 2003/0069635 A1 | 4/2003 | Cartledge et al. |
| 2005/0123582 A1 | 6/2005 | Sung et al. |
| 2005/0137687 A1 | 6/2005 | Salahieh et al. |
| 2005/0203614 A1 | 9/2005 | Forster et al. |
| 2005/0240262 A1 | 10/2005 | White |
| 2006/0020327 A1 | 1/2006 | Lashinski et al. |
| 2008/0288055 A1 | 11/2008 | Paul, Jr. |
| 2010/0049313 A1 | 2/2010 | Alon et al. |
| 2010/0185277 A1* | 7/2010 | Braido .............. A61F 2/2433 623/2.37 |
| 2011/0066224 A1 | 3/2011 | White |
| 2011/0238167 A1 | 9/2011 | Dove et al. |
| 2012/0078356 A1 | 3/2012 | Fish et al. |
| 2012/0277855 A1 | 11/2012 | Lashinski et al. |
| 2013/0018458 A1 | 1/2013 | Yohanan et al. |
| 2013/0184811 A1 | 7/2013 | Rowe et al. |
| 2013/0197631 A1 | 8/2013 | Bruchman et al. |
| 2013/0204360 A1 | 8/2013 | Gainor |
| 2013/0310927 A1 | 11/2013 | Quintessenza |
| 2014/0005772 A1 | 1/2014 | Edelman et al. |
| 2014/0031924 A1 | 1/2014 | Bruchman et al. |
| 2014/0107772 A1 | 4/2014 | Li et al. |
| 2014/0277417 A1 | 9/2014 | Schraut et al. |
| 2014/0324160 A1 | 10/2014 | Benichou et al. |
| 2015/0134056 A1 | 5/2015 | Caliborne, III et al. |
| 2015/0142104 A1 | 5/2015 | Braido |
| 2015/0209141 A1 | 7/2015 | Braido et al. |
| 2015/0216663 A1 | 8/2015 | Braido et al. |
| 2015/0289973 A1 | 10/2015 | Braido et al. |
| 2015/0320556 A1 | 11/2015 | Levi et al. |
| 2016/0128831 A1 | 5/2016 | Zhou et al. |
| 2016/0135951 A1 | 5/2016 | Salahieh et al. |
| 2016/0143732 A1 | 5/2016 | Glimsdale |
| 2016/0158007 A1 | 6/2016 | Centola et al. |
| 2016/0175095 A1 | 6/2016 | Dienno et al. |
| 2016/0220365 A1 | 8/2016 | Backus et al. |
| 2016/0317293 A1 | 11/2016 | Matheny et al. |
| 2016/0331532 A1 | 11/2016 | Quadri |
| 2016/0367360 A1 | 12/2016 | Cartledge et al. |
| 2016/0367364 A1 | 12/2016 | Torrianni et al. |
| 2017/0049566 A1 | 2/2017 | Zeng et al. |
| 2017/0056170 A1 | 3/2017 | Zhu et al. |
| 2017/0119525 A1 | 5/2017 | Rowe et al. |
| 2017/0189174 A1 | 7/2017 | Braido et al. |
| 2017/0258585 A1 | 9/2017 | Marquez et al. |
| 2017/0312075 A1 | 11/2017 | Fahim et al. |
| 2018/0028312 A1 | 2/2018 | Thill et al. |
| 2018/0228603 A1 | 8/2018 | Racchini et al. |
| 2019/0117390 A1* | 4/2019 | Neethling ............... A61L 27/16 |
| 2020/0188099 A1 | 6/2020 | Dvorsky et al. |
| 2021/0212819 A1 | 7/2021 | Reed et al. |
| 2021/0212822 A1 | 7/2021 | Reed et al. |
| 2021/0212823 A1 | 7/2021 | Reed et al. |

FOREIGN PATENT DOCUMENTS

| | | |
|---|---|---|
| EP | 2967869 | 1/2016 |
| EP | 3697343 | 8/2020 |
| JP | 2008-264553 | 11/2008 |
| JP | 2015-519187 | 7/2015 |
| WO | WO 2001/076510 | 10/2001 |
| WO | WO 2003/030776 | 4/2003 |
| WO | WO 2007/013999 | 2/2007 |
| WO | WO 2011/072084 | 6/2011 |
| WO | WO 2011/109450 | 9/2011 |
| WO | WO 2014/164832 | 10/2014 |
| WO | WO 2014/204807 | 12/2014 |
| WO | WO 2015/126712 | 8/2015 |
| WO | WO 2015/173794 | 11/2015 |
| WO | WO 2017/031155 | 2/2017 |
| WO | WO 2019/078979 | 4/2019 |
| WO | WO 2019/144036 | 7/2019 |
| WO | WO 2022/010958 | 1/2022 |

OTHER PUBLICATIONS

International Search Report and Written Opinion in International Appln. No. PCT/US2019/033160, dated Sep. 3, 2019, 9 pages.

International Search Report and Written Opinion in International Appln. No. PCT/US2019/033165, dated Sep. 3, 2019, 12 pages.

International Search Report and Written Opinion in International Appln. No. PCT/US2019/033167, dated Sep. 3, 2019, 9 pages.

International Search Report and Written Opinion in International Appln. No. PCT/US2021/040592 dated Oct. 26, 2021, 9 pages.

Lim et al., "Flat or Curved Pericardial Aortic Valve Cusps: A Finite Element Study," Journal of Heart Valve, Sep. 2004, 13(5):792-7.

* cited by examiner

PROSTHETIC HEART VALVES

CROSS-REFERENCE TO RELATED APPLICATIONS

This application claims the benefit of U.S. patent application Ser. No. 17/957,675 (U.S. Pat. No. 11,622,853) filed Sep. 30, 2022. The disclosure of the prior application is considered part of (and is incorporated by reference in) the disclosure of this application.

BACKGROUND

1. Technical Field

This document relates to devices and methods for the treatment of heart conditions. For example, this document relates to prosthetic heart valves and methods for transcatheter heart valve implantation.

2. Background Information

Cardiac valvular stenosis is a condition in which the heart's valves are narrowed (stenotic). With valvular stenosis, the tissues forming the valve leaflets become stiffer, narrowing the valve opening, and reducing the amount of blood that can flow through it. If the stenosis is mild, the overall cardiac output remains normal. However, when the valves can become severely stenotic, that can lead to a reduction in cardiac output and impairment of heart function.

Aortic valve stenosis affects approximately 5% of all people over age 75 years. Aortic valve stenosis occurs when the heart's aortic valve narrows. When the aortic valve is so obstructed, the heart has to work harder to pump blood to the body. Eventually, this extra work limits the amount of blood the heart can pump, and may weaken the heart muscle. The left atrium may enlarge as pressure builds up, and blood and fluid may then collect in the lung tissue (pulmonary edema), making it hard to breathe. Medications can ease symptoms of mild to moderate aortic valve stenosis. However, the only way to treat severe aortic valve stenosis is by surgery to replace the valve.

Therapies to repair or replace the aortic valve include balloon valvuloplasty (valvotomy), surgical aortic valve replacement, and transcatheter aortic valve replacement (TAVR). TAVR involves replacing the aortic valve with a prosthetic valve that is delivered, for example, via the femoral artery (transfemoral) or the left ventricular apex of the heart (transapical). TAVR is sometimes referred to as transcatheter aortic valve implantation (TAVI).

SUMMARY

This document describes devices and methods for the treatment of heart conditions. For example, this document describes prosthetic heart valves and transcatheter heart valve replacement methods.

In some embodiments, the prosthetic heart valves include a valve member made of a biomaterial that is molded into a specific three-dimensional ("3D") shape. The shape of the molded valve member, as described herein, is especially designed to provide enhanced performance characteristics such as, but not limited to, low mean pressure gradient, low leaflet stress, large open area, high coaptation area, and high duration in an open state, to name a few.

In some embodiments, the prosthetic heart valves include an expandable metallic stent frame surrounding the valve member. Localized protective covering members can be attached to portions of the stent frame to prevent direct contact between the valve member and the stent frame when the valve member is in its open state. Such protective covering members can prolong the life and performance of the valve member by protecting it from direct contact with the metallic stent frame. In addition, a skirt can be attached to the stent frame to cover other portions of the stent frame so that the valve member does not contact those other portions. In some embodiments, the combination of the skirt and the local protective covering members prevent the valve member from directly contacting any portion of the stent frame that is not covered.

In one aspect, this disclosure is directed to a prosthetic heart valve. Such a prosthetic heart valve can include a stent frame that is reconfigurable between a low-profile delivery configuration and an expanded operable configuration, and a valve member attached to the stent frame. The valve member can include three leaflets. Each leaflet of the three leaflets has a free edge and a three-dimensional shape. The three-dimensional shape of the leaflet includes: (i) a first planar region comprising a first free edge portion that terminates at a central location of the free edge of the leaflet, (ii) a second planar region comprising a second free edge portion that terminates at the central location of the free edge of the leaflet, and (iii) a concave region disposed between the first and second planar regions and having a vertex at the central location of the free edge of the leaflet.

Such a prosthetic heart valve can optionally include one or more of the following features. In some embodiments, the valve member is configured to allow blood flow through the prosthetic heart valve from an inflow end of the prosthetic heart valve to an outflow end of the prosthetic heart valve and to prevent blood flow through the prosthetic heart valve from the outflow end to the inflow end. In some embodiments, the valve member extends to an edge of the stent frame at the inflow end. The concave region may interface with the first planar region along a first curved path, and the concave region may interface with the second planar region along a second curved path. The first free edge may be linear and the second free edge may be linear. In some embodiments, the first free edge and the second free edge are non-parallel in relation to each other. An angle may be defined between the first free edge and the second free edge. The angle may be between 80° and 120°. In some embodiments, the first and second planar regions are non-coplanar. The valve member may comprise a biomaterial. In some embodiments, the biomaterial is molded to create the three-dimensional shape.

In another aspect, this disclosure is directed to a prosthetic heart valve that includes a valve member comprising three flexible leaflets and a stent comprising a metal framework that is reconfigurable between a low-profile delivery configuration and an expanded operable configuration. The metal framework includes: (i) three commissure posts to which the valve member is attached; and (ii) three frame portions, each of the three frame portions located between two of the commissure posts. The prosthetic heart valve also includes three separate protective covering members attached to the three frame portions and covering a localized valve-facing surface of each of the three frame portions.

Such a prosthetic heart valve may optionally include one or more of the following features. The three separate protective covering members may comprise bovine pericardium sutured to the three frame portions. The prosthetic heart valve may also include a skirt attached to an inside and an outside of an inflow end of the stent. In some embodiments, the skirt abuts against the protective covering members. The valve member may be configured to allow blood flow through the prosthetic heart valve from an inflow end of the prosthetic heart valve to an outflow end of the prosthetic heart valve and to prevent blood flow through the prosthetic heart valve from the outflow end to the inflow end. The valve member may include three free edges. Each of the three free edges may extend between two of the commissure posts. The valve member may be reconfigurable between a fully closed configuration in which the three free edges are in contact with each other and a fully open configuration in which the three free edges are separated from each other. In the fully open configuration, middle portions of each of the three free edges may be located closer to the inflow end than outflow edges of each of the three separate protective covering members. In the fully closed configuration, all portions of each of the three free edges may be located closer to the outflow end than the outflow edges of each of the three separate protective covering members. In some embodiments, each of the three frame portions is located equidistant between two of the commissure posts.

Particular embodiments of the subject matter described in this document can be implemented to realize one or more of the following advantages. In some embodiments, heart conditions such as valvular stenosis can be treated using the devices and methods provided herein. Some patients who would be too high risk for a traditional surgical valve replacement procedure can be treated using the prosthetic valve devices and transcatheter heart valve replacement methods provided herein. In some embodiments, the valve member of the prosthetic heart valves are shaped in a specific way that enhances various valve performance characteristics. In addition, some embodiments include localized protective covering members attached to particular portions of the stent frame to prevent direct contact between the valve member and the stent frame when the valve member is in its open state. The protection provided by the covering members enhances valve leaflet performance and durability.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

Like reference numbers represent corresponding parts throughout.

DETAILED DESCRIPTION

This document describes devices and methods for the treatment of heart conditions. For example, this document describes prosthetic heart valves and transcatheter heart valve replacement methods.

Figure 1:
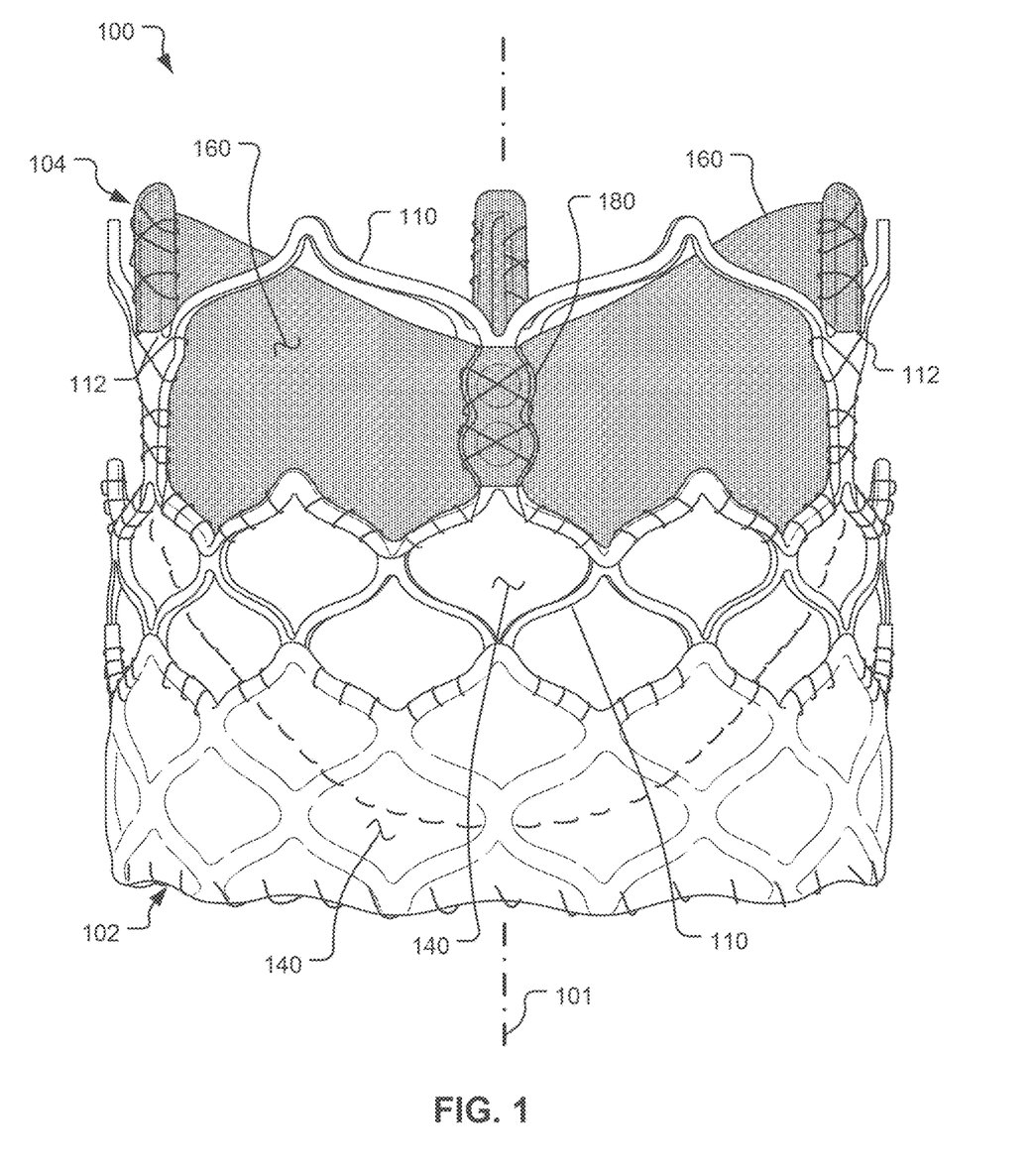
FIG. 1 is a side view of an example prosthetic heart valve in accordance with some embodiments.
Figure 2:
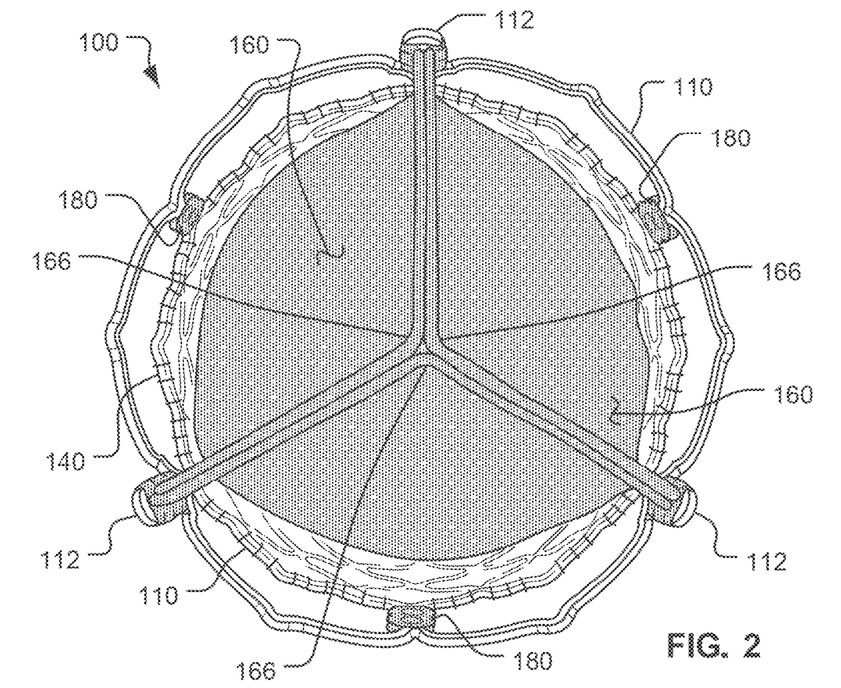
FIG. 2 is a top view of the prosthetic heart valve of FIG. 1 while the valve is in its fully closed configuration.
Figure 3:
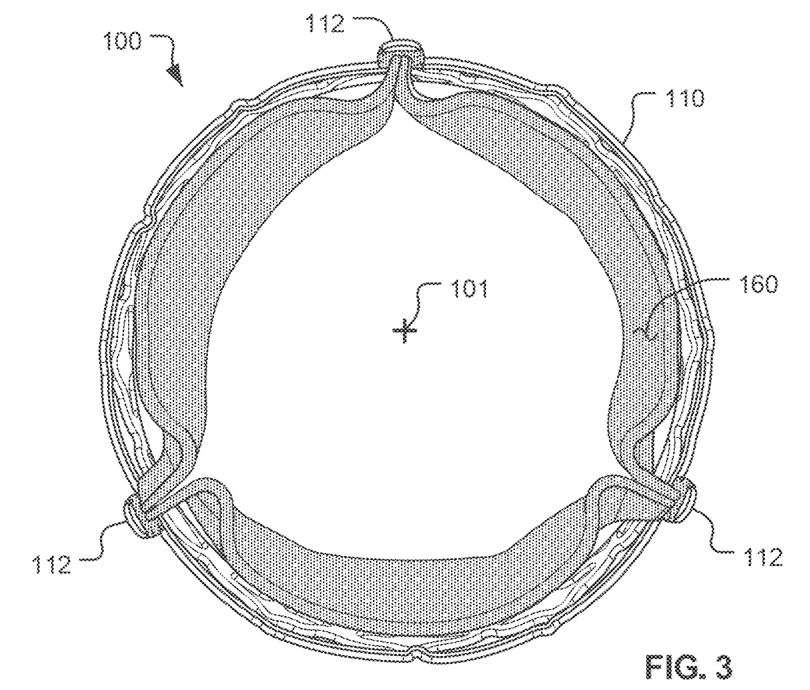
FIG. 3 is a top view of the prosthetic heart valve of FIG. 1 while the valve is in its fully open configuration.

Referring to FIGS. 1-3, an example prosthetic heart valve 100 can be used to replace a native heart valve of a patient. The prosthetic heart valve 100 is particularly well suited for use at a native aortic valve location, but may also be utilized at locations of other native heart valves such as, but not limited to, mitral, pulmonic, and tricuspid valves.

In some cases, the prosthetic heart valve 100 can be deployed using a minimally invasive transcatheter technique. Accordingly, the prosthetic heart valve 100 is radially compactable (e.g., crimped) into a low-profile delivery system configuration for passage through a delivery sheath and into the vasculature of a patient. The delivery system can be percutaneously inserted in a blood vessel (e.g., femoral artery, femoral vein, radial artery, etc.) of the patient, and navigated to the target location using imaging techniques such as fluoroscopy, MRI, or ultrasound. In some circumstances, a guidewire may be installed first. Radiopaque and/or echogenic markers can be included on one or more locations of the prosthetic heart valve 100 for enhanced imaging. At the target location, the prosthetic heart valve 100 can be deployed from the delivery system and then expanded in situ to become positioned at the target location. The prosthetic heart valve 100 may be self-expanding or expandable by a mechanical means such as a balloon. Other access techniques are also envisioned, such as a transapical approach.

FIGS. 1-3 show the prosthetic heart valve 100 in its expanded configuration, after being deployed from delivery system. FIG. 2 shows the prosthetic heart valve 100 in its closed state. FIG. 3 shows the prosthetic heart valve 100 in its open state.

The prosthetic heart valve 100 acts as a one-way valve. That is, the prosthetic heart valve 100 functions to allow blood to flow through the prosthetic heart valve 100 in the direction from an inflow end 102 (FIG. 1) to an outflow end 104. Conversely, the prosthetic heart valve 100 functions to prevent blood from flowing through the prosthetic heart valve 100 in the opposite direction, i.e., from the outflow end 104 to the inflow end 102. To be clear, FIGS. 2 and 3 are views of the outflow end 104. The prosthetic heart valve 100 also defines a central longitudinal axis 101.

The prosthetic heart valve 100 includes a stent frame 110, a skirt 140, a valve member 160, and protective covering members 180. The skirt 140 is attached to the stent frame 110 to cover certain inside and outside portions of the stent frame 110. In the depicted embodiment, the skirt 140 is attached to the stent frame 110 by sutures that are used to stitch the skirt 140 to itself (while also capturing portions of the stent frame 110). As described further below, in some embodiments the skirt 140 is a single unitary piece of covering material. Alternatively, in some embodiments the skirt 140 is made from two or more separate portions of covering material.

The valve member 160 is positioned within the interior of the stent frame 110 and is attached to the stent frame 110 at three commissure posts 112. The protective covering members 180 are also attached to the stent frame 110. In particular, in the depicted embodiment the protective covering members 180 are attached to the stent frame 110 at three locations of the stent frame 110 that each bisect the locations of the commissure posts 112. In some embodiments, the stent frame 110 may include additional portions between the commissure posts 112 and additional protective covering members 180 may be attached to the additional portions.

The stent frame 110 is a generally cylindrical arrangement of elongate members and the three commissure posts 112. In the depicted embodiment of the stent frame 110, the elongate members are arranged in a cellular manner. That is, the elongate members define multiple open cells. The stent frame 110 may be constructed from stainless steel, shape memory alloys, plastically deformable alloys, or combinations thereof. Examples of such alloy materials include, but are not limited to, nickel-titanium alloys such as NITINOL® alloys, cobalt-chromium alloys such as ELGILOY® alloys, platinum-tungsten alloys, tantalum alloys, and so forth. Other alloys that may be employed in making the stent frame 110 include, but are not limited to, other cobalt-chromium alloys, titanium cobalt-chromium molybdenum alloys, and so forth. In addition to these materials, the stent frame 110 may further be constructed from polymers, biomaterials, or combinations thereof. In some embodiments, the stent frame 110 can originally be a tube (e.g., a NITINOL® or ELGILOY® tube) that is laser cut and expanded into to the desired open cylindrical configuration, and heat-set to make the cylinder the natural configuration of elongate members.

In some embodiments, the elongate members of the stent frame 110 can be wires that are wound, woven, and/or attached together (e.g., welded or glued) to create the cylindrical configuration.

In some embodiments, the stent frame 110 may have a coating on at least a portion of one of either the exterior surface or the interior surface. The coating may comprise a polymer, including but not limited to polytetrafluoroethylene (PTFE), silicone, biopolymers and other suitable polymers. In other embodiments, the coating may comprise a radiopaque material. In some embodiments, the coating may comprise a drug eluting material.

The prosthetic heart valve 100 also includes the skirt 140. The skirt 140 is a covering on all or on some areas of stent frame 110. In the depicted embodiment, the skirt 140 is a single unitary piece of covering material that is wrapped around the inflow end 102 of the stent frame 110 to cover portions of the inside of the stent frame 110 and portions of the outside of the stent frame 110. Alternatively, in some embodiments the skirt 140 is made from two or more separate portions of covering material. For example, in some embodiments a first portion of the skirt 140 can be used to cover at least portions of the inside of the stent frame 110 and a second, separate portion of the skirt 140 can be used to cover at least portions of the outside of the stent frame 110. In some such embodiments, the inside portion of the skirt 140 can be made of a type of material that differs from the type of material used for the outside portion of the skirt 140. In particular embodiments, the skirt 140 can be made of materials including, but not limited to, Dacron, polyester fabrics (e.g., PVL), polyethylene terephthalate (PET), Teflon-based materials, Polytetrafluoroethylene (PTFE), expanded Polytetrafluoroethylene (ePTFE), polyurethanes, silicone, Bio A, copolymers, film or foil materials, or combinations of the foregoing materials and/or like materials. In some embodiments, the skirt 140 has a material composition and configuration that inhibits or prevents tissue ingrowth to the skirt 140. In some embodiments, the skirt 140, or portions thereof, has a microporous structure that provides a tissue ingrowth scaffold for durable sealing and supplemental anchoring strength of the prosthetic heart valve 100.

The skirt 140 can be attached to stent frame 110 in a variety of suitable manners. For example, in some embodiments, the skirt 140 is sewn to the elongate members of the stent frame 110. In some embodiments, the skirt 140 is glued to the stent frame 110. In some embodiments, portions of the stent frame 110 are sandwiched between two layers of the skirt 140 that are sutured together. In some embodiments, a combination of such attachment methods are used. These and all other variations of frame member types, material compositions, material treatments, configurations, fabrication techniques, and methods for attaching the skirt 140 to the stent frame 110 are envisioned and within the scope of the disclosure provided herein.

The prosthetic heart valve 100 also includes the valve member 160. The valve member 160 may comprise a tissue material. In some embodiments, the tissue material may be a biomaterial. In some embodiments, the tissue material may be a cross-linked collagen-based biomaterial that comprises acellular or cellular tissue selected from the group consisting of cardiovascular tissue, heart tissue, heart valve, aortic roots, aortic wall, aortic leaflets, pericardial tissue, connective tissue, dura mater, dermal tissue, vascular tissue, cartilage, pericardium, ligament, tendon, blood vessels, umbilical tissue, bone tissue, fasciae, and submucosal tissue and skin. In some embodiments, the tissue material is an implantable biomaterial such as the biomaterial described in the disclosure of U.S. Pat. No. 9,205,172, filed on Dec. 21, 2005, and entitled "Implantable Biomaterial and Method of Producing Same," which is incorporated by reference herein in its entirety. In some embodiments, the cross-linked collagen-based biomaterial is treated with the ADAPT® treatment process, which is an anti-calcification treatment process for biomaterials that leaves zero residual DNA and has over ten years of clinical data demonstrating no calcification when used in cardiac surgeries. In some embodiments, the tissue material may be artificial tissue. In some embodiments, the artificial tissue may comprise a single piece molded or formed polymer. In some embodiments, the artificial tissue may comprise polytetrafluoroethylene, isotropic silicone, polyethylene terephthalate, other polymers, and other polymer coatings.

As described further below, in some embodiments the valve member 160 may comprise shaped tissue material. More particularly, at least some or all of the leaflets of the valve member 160 may comprise shaped tissue material (e.g., shaped using a mold and the ADAPT® treatment process). In some embodiments, the valve member 160 is a single-piece three-dimensional valve constructed from a single piece of tissue material as described further below.

The valve member 160 is joined to itself in a manner that captures the three commissure posts 112 and thereby attaches the valve member 160 to the stent frame 110 at the three commissure posts 112. In some embodiments, valve member 160 has slits in which the three commissure posts 112 are received. This is described, for example, in Application PCT/US2021/040596 filed on Jul. 7, 2021, which is hereby incorporated by reference in its entirety. Such a joining technique allows for a large diameter opened state (as depicted in FIGS. 3) and also reduces leaflet stresses at the point of attachment. The valve member 160 can be attached to itself and/or to the three commissure posts 112 by means such as by suturing, using mechanical clips, sewing, using hooks or barbs, using adhesives, bonding, a mechanical channel, and by combinations thereof.

The prosthetic heart valve 100 also includes the protective covering members 180. In the depicted embodiment, three protective covering members 180 are included. In some embodiments, fewer than three or more than three protective covering members 180 can be included. The protective covering members 180 are localized covering materials that are attached at particular locations on the stent frame 110. The primary purpose of the protective covering members 180 is to inhibit or prevent the valve member 160 from contacting the stent frame 110 when the valve member 160 reconfigures to its open state (e.g., as shown in FIG. 3). By protecting the valve member 160 in that manner, the useful life of the valve member 160 can be extended.

In fact, in the depicted embodiment, no portion of the valve member 160 directly contacts the stent frame 110 (other than where the valve member 160 is attached to the stent frame at the three commissure posts 112). The skirt 140 and the protective covering members 180 are contacted by the valve member 160, and the skirt 140 and the protective covering members 180 thereby serve to prevent the valve member 160 from directly contacting the stent frame 110. In the depicted embodiment, and as best seen in FIG. 1, an upper edge of the skirt 140 abuts a lower edge of each of the protective covering members 180. Accordingly, the inner surface of the stent frame 110 is fully covered in those areas.

In some embodiments, the protective covering members 180 are patches made of bovine pericardium that are sutured to the stent frame 110. In some embodiments, the protective covering members 180 are made of any other suitable biomaterial or synthetic material, such as the materials described above about the skirt 140 or the valve member 160, and/or combinations of such materials. For example, in some embodiments the protective covering members 180 comprise bovine pericardium on the inside of the stent frame 110 and PET on the outside of the stent frame 110.

Figure 4:
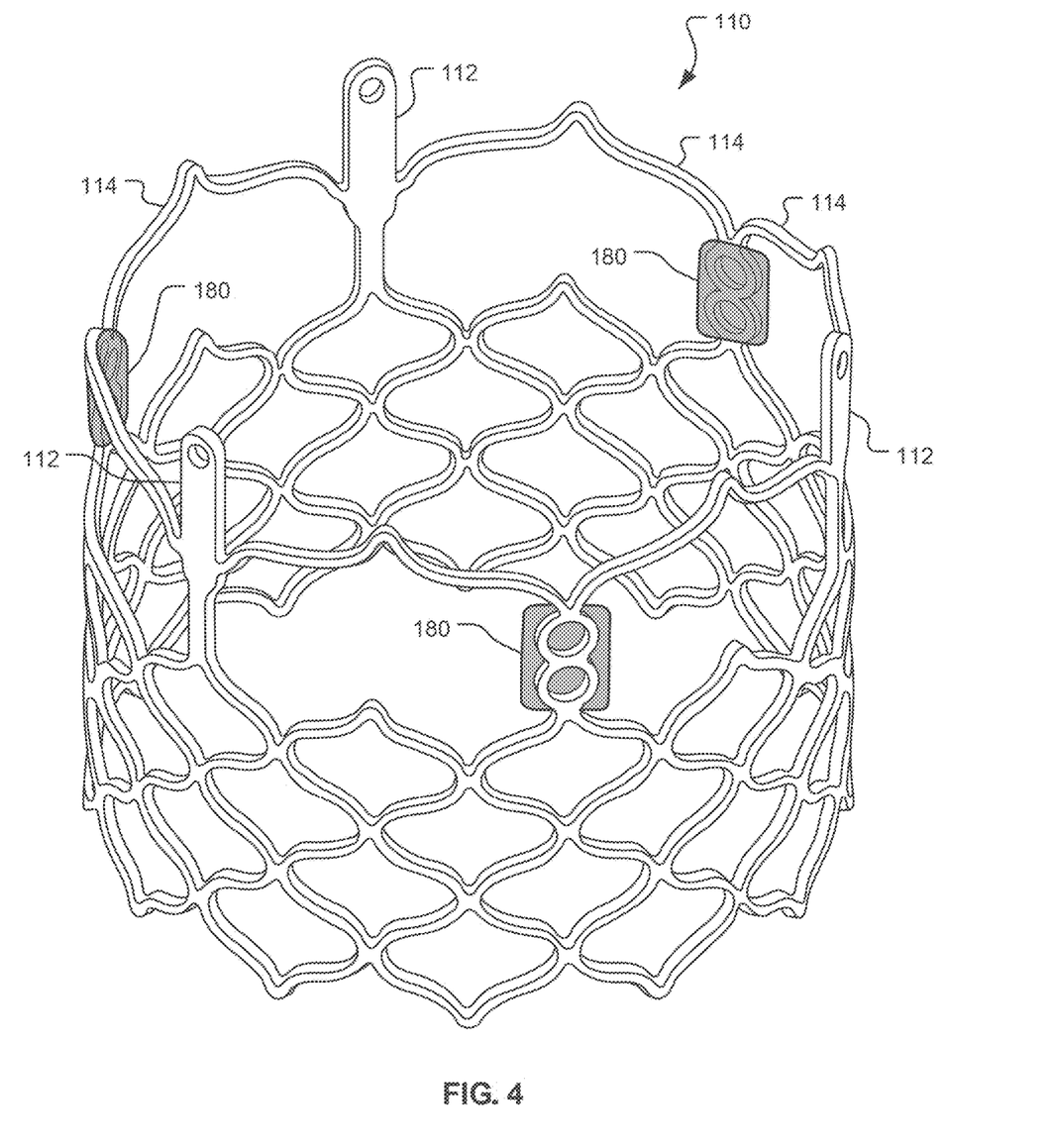
FIG. 4 is a perspective view of an example stent or metallic framework of the prosthetic heart valve of FIG. 1.

Referring also to FIG. 4, here an isolated view of the stent frame 110 (without the skirt 140 and valve member 160) and the protective covering members 180 is provided. The protective covering members 180 are shown in their particular locations on the inside of the stent frame 110. It can be seen that the protective covering members 180 are located on three portions of the stent frame 110 that are each located equidistant between two of the commissure posts 112. The three separate protective covering members 180 are attached to the three frame portions to cover a localized valve-facing surface of each of the three frame portions of the stent frame 110.

The valve member 160 includes three free edges that extend between the three commissure posts 112 and that coapt (make contact) with each other when the valve member 160 is in its closed configuration (e.g., as shown in FIG. 2), and that spread apart from each other when the valve member 160 is in its open configuration (e.g., as shown in the fully open configuration of FIG. 3). The protective covering members 180 serve to protect the valve member 160 (including, in particular, middle portions of the free edges of the valve member 160) from directly contacting the stent frame 110 when the valve member 160 is in its fully open configuration.

In the fully open configuration, the middle portions of each of the three free edges of the valve member 160 are located closer to the inflow end 102 than the edges closest to the outflow end 104 of each of the three separate protective covering members 180. Put another way, when the valve member 160 is in its open configuration, the middle portions of each of the three free edges of the valve member 160 are below (closer to the inflow end 102) than the top edges (or "outflow edges" because they are closer to the outflow end 104) of the protective covering members 180. This arrangement helps to ensure that the free edges of the valve member 160 are prevented by the protective covering members 180 from directly contacting the stent frame 110 when the valve member 160 is in its fully open configuration.

As best seen in FIG. 4, in the depicted embodiment the protective covering members 180 are attached to portions of the stent frame 110 that are directly connected to adjacent commissure posts 112 by two elongate members 114 that extend in opposite directions like arches. That is, two elongate members 114 extend from each portion of the stent frame 110 to which a protective covering member 180 is attached. One of those two elongate members 114 extends directly to a first commissure post 112 and the other of those two elongate members 114 extends directly to a second commissure post 112, wherein the protective covering member 180 bisects the positions of the first and second commissure posts 112. Because the elongate members 114 extend directly between the commissure posts 112 and the portions of the stent frame 110 to which the protective covering members 180 are attached, large open cells are defined by the stent frame 110 between the protective covering members 180 and the commissure posts 112.

Figure 5:
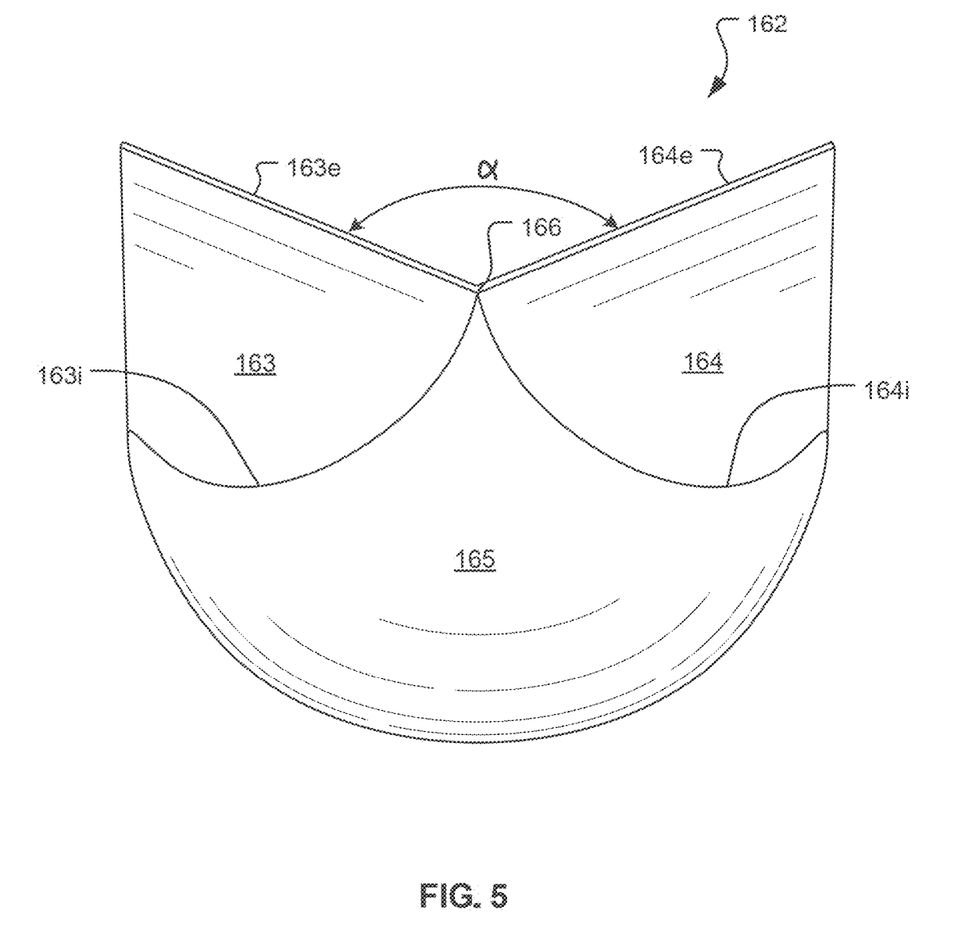
FIG. 5 is a plan view of an example leaflet portion of a valve member of the prosthetic heart valve of FIG. 1.

Referring also to FIG. 5, the valve member 160 is made up of three leaflets 162. FIG. 5 illustrates an example of a single leaflet 162 so that its particular shape can be clearly envisioned. The leaflets 162 make up the portions of the valve member 160 that extend between the commissure posts 112 of the stent frame 110. The leaflets 162 are the portions of the valve member 160 that do most or all of the reconfiguring movements when the valve member 160 cycles between its closed and fully open configurations (e.g., as shown in FIGS. 2 and 3).

The leaflet 162 depicted in FIG. 5 is shown in two dimensions, but the natural shape of the leaflet 162 (in an unstressed state) is actually three-dimensional. That is, the leaflet 162 includes a first planar region 163, a second planar region 164, and a concave region 165. The first planar region 163 and the second planar region 164 are each planar (but not in the plane of the paper of FIG. 5). The concave region 165 is concaved, contoured, dish-shaped, etc. The concave region 165 is disposed between the first planar region 163 and the second planar region 164. The first planar region 163 and the second planar region 164 are non-coplanar with each other. That is, the first planar region 163 defines a first plane and the second planar region 164 defines a second plane that is different from the first plane. The extended planes defined by the first planar region 163 and the second planar region 164 intersect each other.

The first planar region 163 and the second planar region 164 include the free edges of the leaflet 162. The first planar region 163 includes a first free edge portion 163e, and the second planar region 164 includes a second free edge portion 164e. The first free edge portion 163e and the second free edge portion 164e together make up the free edge of the leaflet 162.

The first free edge portion 163e meets the second free edge portion 164e at a central location 166 of the free edge of the leaflet 162. The first free edge portion 163e and the second free edge portion 164e are each linear in the depicted embodiment, but they are not collinear in relation to each other. Neither are the first free edge portion 163e and the second free edge portion 164e parallel in relation to each other. Rather, an angle "a" is defined between the first free edge portion 163e and the second free edge portion 164e. In some embodiments, the angle α is in a range of between 80° to 120°, or between 70° to 130°, or between 90° to 110°, or between 100° to 140°, without limitation.

The concave region 165 is disposed between the first planar region 163 and the second planar region 164. The concave region 165 interfaces with the first planar region 163 along a first curved path 163i. The concave region 165 interfaces with the second planar region 164 along a second curved path 164i. The first curved path 163i extends to the central location 166 of the free edge of the leaflet 162. The second curved path 164i also extends to the central location 166 of the free edge of the leaflet 162. The first curved path 163i meets the second curved path 164i at the central location 166 of the free edge of the leaflet 162. Accordingly, it can be said that the concave region 165 includes a vertex that is positioned at the central location 166 of the free edge of the leaflet 162.

Figure 6:
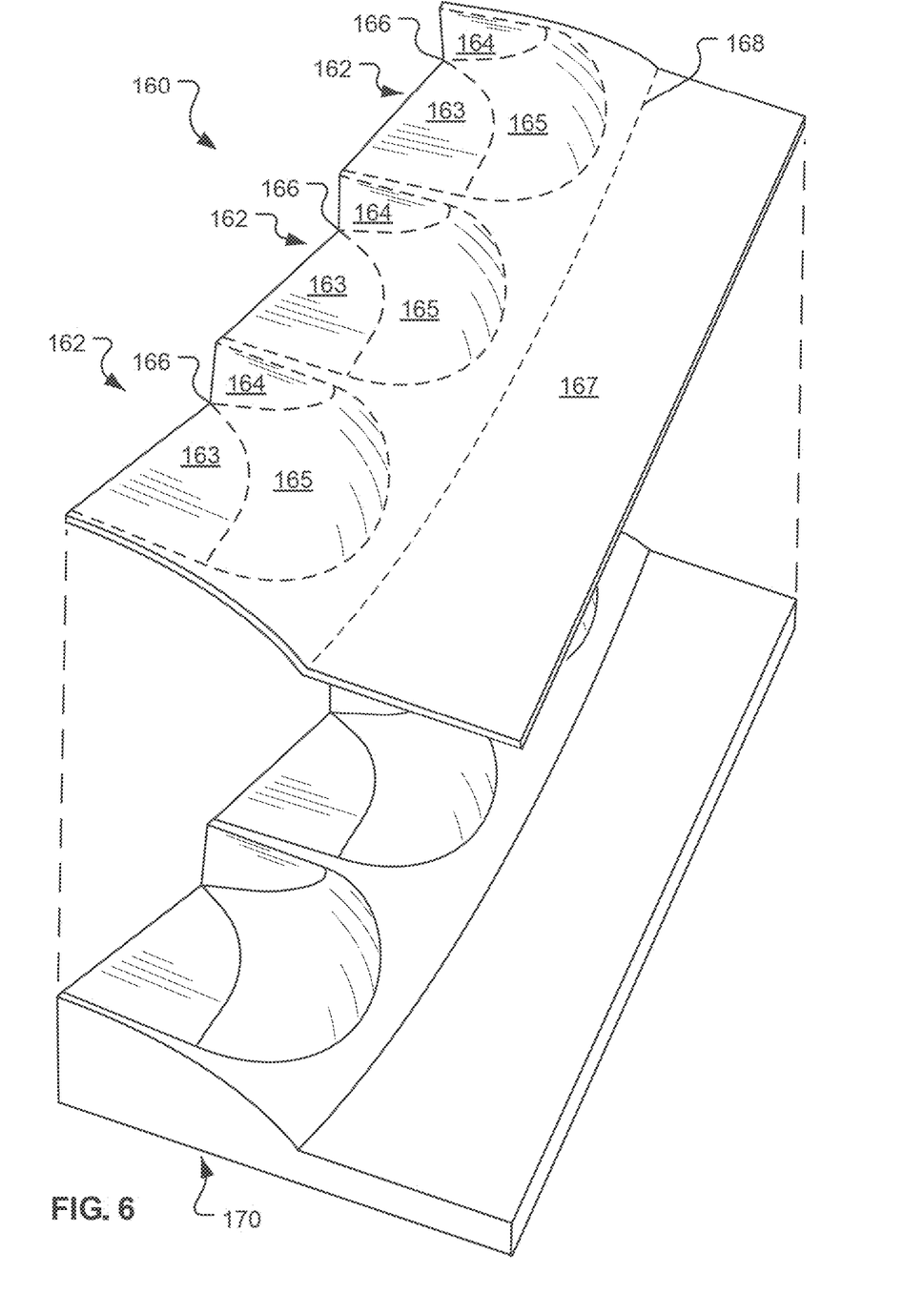
FIG. 6 depicts a mold and a resulting molded valve member of the prosthetic heart valve of FIG. 1.

FIG. 6 illustrates one manner in which a valve member 160 having three leaflets 162 can be fabricated. In this example, the material of the valve member 160 is formed to have the three-dimensional shape of the leaflets 162 as described above using a mold 170. Here, half of the mold 170 is shown, while the other half of the mold 170 is not shown for simplicity. Such a mold 170 can be used to form the material of the valve member 160 to have three leaflets 162 with the first planar region 163, the second planar region 164, and the concave region 165. In some embodiments, the mold 170 can include apertures, channels, ports, or be made of a porous material so that fluid can pass through the mold 170 to reach the tissue material during the tissue molding process.

In addition to the leaflets 162, the valve member 160 can optionally include a base portion 167. In the depicted embodiment, there is a delineation 168 between the base portion 167 and the portion of the valve member 160 that includes the leaflets 162. Alternatively, in some embodiments the base portion 167 is simply a direct extension of the portion of the valve member 160 that includes the leaflets 162 (without having a distinct delineation 168). In some embodiments, the valve member 160 is attached to the stent frame 110 so that the base portion 167 extends all the way to an edge of the stent frame 110 at the inflow end 102 of the prosthetic heart valve 100.

After forming the three-dimensional shape of the valve member 160 as depicted in FIG. 6, the valve member 160 can be formed into a generally cylindrical shape within the stent frame 110.

Figures 7, 8:
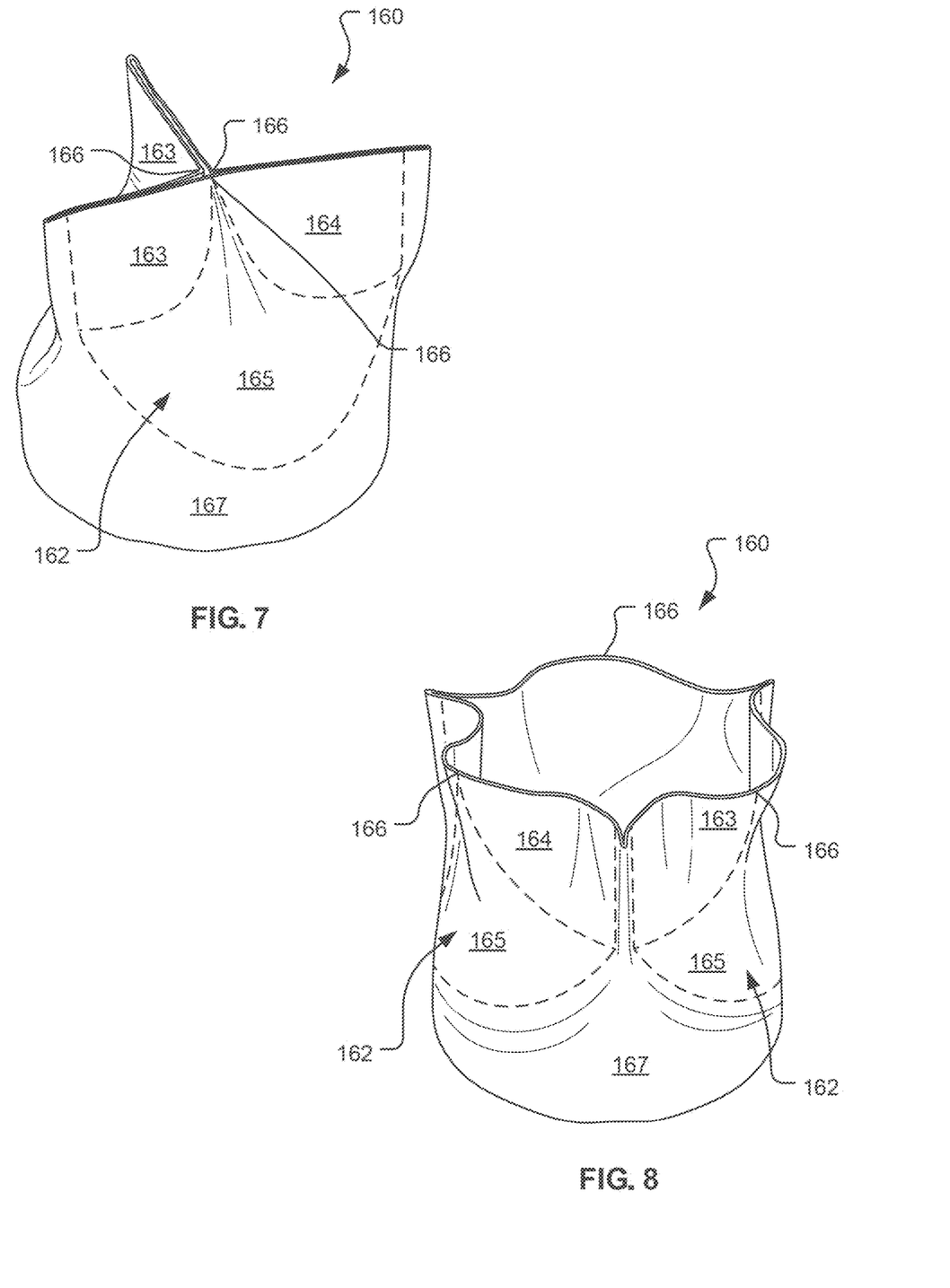
FIG. 7 depicts the valve member of FIG. 6 in a fully closed state.
FIG. 8 depicts the valve member of FIG. 6 in a fully open state.

FIGS. 7 and 8 show the valve member 160 in closed and fully open configurations, respectively. Here, the stent frame 110 and other portions of the prosthetic heart valve 100 are not shown so that the shape features of the valve member 160 can be more readily visualized.

The shape features of the valve member 160 (e.g., the leaflets 162 that include the first planar region 163, the second planar region 164, and the concave region 165), and how those shape features are arranged on the valve member 160 as described in reference to FIG. 5 in particular, have been designed and selected by the inventors to achieve certain advantageous performance characteristics for the prosthetic heart valve 100. For example, the shape features of the valve member 160 enhance performance features of the prosthetic heart valve 100 such as, but not limited to, high leaflet coaptation area, low mean pressure gradient, large valve open area, low leaflet stress, and high duration of the valve 160 in its open state.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking may be advantageous.

What is claimed is:

1. A prosthetic heart valve comprising:
   a stent frame that is reconfigurable between a low-profile delivery configuration and an expanded operable configuration; and
   a valve member comprising a single piece of collagen-based biomaterial attached to the stent frame and comprising multiple leaflets, wherein each leaflet has a free edge and is molded and cross-linked to retain a three-dimensional shape comprising a concave region, wherein the prosthetic heart valve includes an inflow end and an outflow end, wherein the valve member is configured to: (i) open to allow blood flow from the inflow end to the outflow end and (ii) close to prevent blood flow from the outflow end to the inflow end, and wherein the concave region of each leaflet is spaced apart from an edge of the stent frame at the inflow end by portions of the collagen-based biomaterial that are molded to be non-planar.

2. The prosthetic heart valve of claim 1, wherein the concave region of each leaflet has a vertex at a central location of the free edge of the leaflet.

3. The prosthetic heart valve of claim 1, wherein each leaflet further comprises:
   a first planar region comprising a first free edge portion that terminates at a central location of the free edge of the leaflet; and
   a second planar region comprising a second free edge portion that terminates at the central location of the free edge of the leaflet, and wherein the concave region is disposed between the first and second planar regions.

4. The prosthetic heart valve of claim 3, wherein the first free edge is linear and the second free edge is linear.

5. The prosthetic heart valve of claim 4, wherein the first free edge and the second free edge are non-parallel in relation to each other.

6. The prosthetic heart valve of claim 4, wherein an angle defined between the first free edge and the second free edge is between 80° and 120°.

7. The prosthetic heart valve of claim 3, wherein the first and second planar regions are non-coplanar.

8. A prosthetic heart valve comprising:
a valve member comprising flexible leaflets;
a metal framework comprising: (i) multiple cells, (ii) commissure posts to which the valve member is attached, and (iii) frame portions defining one or more openings that are smaller than the multiple cells;
a skirt attached to an inflow end of the metal framework; and
protective covering members attached to and covering a localized valve-facing surface of the frame portions, wherein the protective covering members are separate from the skirt,
wherein the each of the frame portions is directly connected to two adjacent commissure posts by two individual elongate members of the metal framework that extend in opposite directions like arches.

9. The prosthetic heart valve of claim 8, wherein the skirt defines a cylinder, and wherein the commissure posts and the frame portions all extend from the cylinder toward an outflow end of the metal framework.

10. The prosthetic heart valve of claim 9, wherein the multiple cells comprise multiple small cells and multiple larger cells, wherein skirt is attached to the multiple small cells to define the cylinder, and wherein each of the frame portions are located between two of the commissure posts to thereby define two larger cells of the multiple larger cells.

11. The prosthetic heart valve of claim 9, wherein the multiple larger cells are not covered by the skirt.

12. The prosthetic heart valve of claim 8, wherein the protective covering members comprise three separate protective covering members comprising bovine pericardium sutured to the frame portions.

13. The prosthetic heart valve of claim 8, wherein the skirt abuts against the protective covering members.

14. The prosthetic heart valve of claim 8, wherein the skirt comprises:
a first skirt material attached to an inside of the metal framework; and
a second skirt material attached to an outside of the metal framework, and
wherein the first and second skirt materials are differing types of materials.

15. The prosthetic heart valve of claim 8, wherein the valve member comprises three leaflets that each include a free edge, wherein each of the free edges extends between two of the commissure posts.

16. The prosthetic heart valve of claim 15, wherein the valve member is reconfigurable between a fully closed configuration in which the free edges are in contact with each other and a fully open configuration in which the free edges are separated from each other.

17. The prosthetic heart valve of claim 16, wherein, in the fully open configuration, middle portions of each of the free edges are located closer to the inflow end than outflow edges of each of the protective covering members.

18. The prosthetic heart valve of claim 17, wherein, in the fully closed configuration, all portions of each of the free edges are located closer to the outflow end than the outflow edges of each of the protective covering members.

19. The prosthetic heart valve of claim 8, wherein each of the frame portions are located equidistant between two of the commissure posts.

20. A prosthetic heart valve comprising:
a valve member comprising flexible leaflets;
a metal framework comprising: (i) multiple cells, (ii) commissure posts to which the valve member is attached, and (iii) frame portions defining one or more openings that are smaller than the multiple cells;
a skirt attached to an inflow end of the metal framework, the skirt comprising:
a first skirt material attached to an inside of the metal framework; and
a second skirt material attached to an outside of the metal framework,
wherein the first and second skirt materials are differing types of materials; and
protective covering members attached to and covering a localized valve-facing surface of the frame portions, wherein the protective covering members are separate from the skirt.

21. The prosthetic heart valve of claim 20, wherein the each of the frame portions is directly connected to two adjacent commissure posts by two individual elongate members of the metal framework that extend in opposite directions like arches.

22. The prosthetic heart valve of claim 20, wherein the skirt defines a cylinder, and wherein the commissure posts and the frame portions all extend from the cylinder toward an outflow end of the metal framework.

23. The prosthetic heart valve of claim 22, wherein the multiple cells comprise multiple small cells and multiple larger cells, wherein skirt is attached to the multiple small cells to define the cylinder, and wherein each of the frame portions are located between two of the commissure posts to thereby define two larger cells of the multiple larger cells.

24. The prosthetic heart valve of claim 22, wherein the multiple larger cells are not covered by the skirt.

25. The prosthetic heart valve of claim 20, wherein the protective covering members comprise three separate protective covering members comprising bovine pericardium sutured to the frame portions.

26. The prosthetic heart valve of claim 20, wherein the skirt abuts against the protective covering members.

27. The prosthetic heart valve of claim 20, wherein the valve member comprises three leaflets that each include a free edge, wherein each of the free edges extends between two of the commissure posts.

28. The prosthetic heart valve of claim 27, wherein the valve member is reconfigurable between a fully closed configuration in which the free edges are in contact with each other and a fully open configuration in which the free edges are separated from each other.

29. The prosthetic heart valve of claim 28, wherein, in the fully open configuration, middle portions of each of the free edges are located closer to the inflow end than outflow edges of each of the protective covering members.

30. The prosthetic heart valve of claim 29, wherein, in the fully closed configuration, all portions of each of the free edges are located closer to the outflow end than the outflow edges of each of the protective covering members.

31. The prosthetic heart valve of claim 20, wherein each of the frame portions are located equidistant between two of the commissure posts.

32. A prosthetic heart valve comprising:
   a valve member comprising three flexible leaflets;
   a metal framework comprising: (i) multiple cells, (ii) commissure posts to which the valve member is attached, and (iii) frame portions defining one or more openings that are smaller than the multiple cells;
   a skirt attached to an inflow end of the metal framework; and
   protective covering members attached to and covering a localized valve-facing surface of the frame portions, wherein the protective covering members are separate from the skirt,
   wherein each leaflet of the three flexible leaflets includes a free edge, wherein each of the free edges extends between two of the commissure posts,
   wherein the valve member is reconfigurable between a fully closed configuration in which the free edges are in contact with each other and a fully open configuration in which the free edges are separated from each other,
   wherein, in the fully open configuration, middle portions of each of the free edges are located closer to the inflow end than outflow edges of each of the protective covering members, and
   wherein, in the fully closed configuration, all portions of each of the free edges are located closer to the outflow end than the outflow edges of each of the protective covering members.

33. The prosthetic heart valve of claim 32, wherein the each of the frame portions is directly connected to two adjacent commissure posts by two individual elongate members of the metal framework that extend in opposite directions like arches.

34. The prosthetic heart valve of claim 32, wherein the skirt defines a cylinder, and wherein the commissure posts and the frame portions all extend from the cylinder toward an outflow end of the metal framework.

35. The prosthetic heart valve of claim 34, wherein the multiple cells comprise multiple small cells and multiple larger cells, wherein skirt is attached to the multiple small cells to define the cylinder, and wherein each of the frame portions are located between two of the commissure posts to thereby define two larger cells of the multiple larger cells.

36. The prosthetic heart valve of claim 34, wherein the multiple larger cells are not covered by the skirt.

37. The prosthetic heart valve of claim 32, wherein the protective covering members comprise three separate protective covering members comprising bovine pericardium sutured to the frame portions.

38. The prosthetic heart valve of claim 32, wherein the skirt abuts against the protective covering members.

39. The prosthetic heart valve of claim 32, wherein the skirt comprises:
   a first skirt material attached to an inside of the metal framework; and
   a second skirt material attached to an outside of the metal framework, and
   wherein the first and second skirt materials are differing types of materials.

40. The prosthetic heart valve of claim 32, wherein each of the frame portions are located equidistant between two of the commissure posts.

\* \* \* \* \*